United States Patent
Mattanovich et al.

(10) Patent No.: US 8,962,277 B2
(45) Date of Patent: Feb. 24, 2015

(54) PRODUCTION CELL LINE

(75) Inventors: Diethard Mattanovich, Vienna (AT); Martin Dragosits, Vienna (AT); Brigitte Gasser, Vienna (AT); Michael Maurer, Vienna (AT); Michael Sauer, Vienna (AT)

(73) Assignee: Univeristät für Bodenkultur Wien, Vienna (AT)

( * ) Notice: Subject to any disclaimer, the term of this patent is extended or adjusted under 35 U.S.C. 154(b) by 18 days.

(21) Appl. No.: 13/808,380

(22) PCT Filed: Jul. 4, 2011

(86) PCT No.: PCT/EP2011/061241
§ 371 (c)(1),
(2), (4) Date: Feb. 12, 2013

(87) PCT Pub. No.: WO2012/004226
PCT Pub. Date: Jan. 12, 2012

(65) Prior Publication Data
US 2013/0137141 A1    May 30, 2013

(30) Foreign Application Priority Data
Jul. 5, 2010 (EP) .................................... 10168446

(51) Int. Cl.
| | | |
|---|---|---|
| *C12P 21/04* | (2006.01) | |
| *C12P 1/02* | (2006.01) | |
| *C12N 15/00* | (2006.01) | |
| *C12N 15/74* | (2006.01) | |
| *C12N 15/81* | (2006.01) | |
| *C12N 15/67* | (2006.01) | |
| *C12N 15/80* | (2006.01) | |
| *C12P 21/02* | (2006.01) | |

(52) U.S. Cl.
CPC .............. *C12N 15/815* (2013.01); *C12N 15/67* (2013.01); *C12N 15/80* (2013.01); *C12P 21/02* (2013.01)
USPC .......... 435/70.1; 435/171; 435/440; 435/476; 435/483

(58) Field of Classification Search
None
See application file for complete search history.

(56) References Cited

FOREIGN PATENT DOCUMENTS

| | | |
|---|---|---|
| KR | 100254810 | 5/2000 |
| WO | WO 01/29073 | 4/2001 |
| WO | WO 02/16590 | 2/2002 |
| WO | WO 02/099100 | 12/2002 |

OTHER PUBLICATIONS

Alberghina et al., Systems biology of the cell cycle of *Saccharomyces cerevisiae*: From network mining to system-level properties, Biotechnology Advances, 27:960-978 (2009).
Buchetics et al., Reverse Engineering of Protein Secretion by Uncoupling of Cell Cycle Phases from Growth, Biotechnology and Bioengineering, 108(10):2403-2412 (2011).
Cherlet et al., Surface IgG Content of Murine Hybridomas: Direct Evidence for Variation of Antibody Secretion Rates During the Cell Cycle, Biotechnology and Bioengineering, 47(5):535-540 (1995).
Cross et al., Quantitative Characterization of a Mitotic Cyclin Threshold Regulating Exit from Mitosis, Molecular Biology of the Cell, 16:2129-2138 (2005.
Dragosits et al., The Effect of Temperature on the Proteome of Recombinant *Pichia pastoris*, J. Proteome Res., 8(3):1380-1392 (2009).
Extended European Search Report for Application No. 10168446.2 dated Dec. 22, 2010.
Gasser et al., Protein folding and conformational stress in microbial cells producing recombinant proteins: a host comparative overview, Microbial Cell Factories, 7:1-18 (2008).
International Search Report and Written Opinion for Application No. PCT/EP2011/061241 dated Sep. 15, 2011.
International Preliminary Report on Patentability for Application No. PCT/EP2011/061241 dated Jan. 17, 2013.
Kurtzman, Description of *Komagataella phaffii* sp. nov. and the transfer of *Pichia pseudopastoris* to the methylotrophic yeast genus *Komagataella*, Int. J. Systematic and evol. Microbiology, 55:973-976 (2005.
Marx et al., Overexpression of the riboflavin biosynthetic pathway in *Pichia pastoris*, Microbial Cell Factories, 7(23):1 (2008).
Maurer et al., Versatile modeling and optimization of fed batch processes for the production of secreted heterologous proteins with *Pichia pastoris*, Microbial Cell Factories, 5:37 (2006).
Uchiyama et al., Cell Cycle Dependency of Rice α-Amylase Production in a Recombinant Yeast, Biotech. and Bioengineering, 54:262-271(1997).
Uchiyama et al., Modeling and optimization of a-Amylase Production in a Recombinant yeast fed-bath culture taking account of the cell cycle population distribution, J. Biotechnol., 71:133-141 (1999).
Zhang et al., Maximization of Production of Secreted Recombinant Proteins in *Pichia pastoris* Fed-Batch Fermentation, Biotechnol. Prog. 21:383-393 (2005).

*Primary Examiner* — Suzanne M Noakes
*Assistant Examiner* — Jae W Lee
(74) *Attorney, Agent, or Firm* — Meunier Carlin & Curfman, LLC

(57) ABSTRACT

The invention refers to a method of producing a recombinant polypeptide of interest (POI) in a cell culture, comprising genetically engineering a eukaryotic cell line—to specifically cause prolongation of the G2+M cell cycle phase in a pre-culture phase, and—to produce the POI in a producing phase following the pre-culture phase, a high producer cell line and cell culture as well as a method of increasing the yield of a recombinant POI production in a cell culture.

11 Claims, 4 Drawing Sheets

PRODUCTION CELL LINE

The invention relates to a method of preparing a high producer cell line for producing a polypeptide of interest (POI) in a cell culture.

BACKGROUND

The development of the recombinant DNA techniques has permitted the use of several microorganisms as host for the expression of heterologous proteins with pharmaceutical and industrial application.

Many different host cells are used today for the production of such heterologous proteins. Successful production of recombinant proteins has been accomplished with eukaryotic hosts. The most prominent examples are budding yeasts like *Saccharomyces cerevisiae*, *Pichia pastoris* or *Hansenula polymorpha*, filamentous fungi like *Aspergillus awamori* or *Trichoderma reesei*, or mammalian cells like e.g. CHO cells.

Yeasts are attractive hosts for the production of recombinant proteins and small metabolites. *Pichia pastoris*, a methylotrophic yeast, is frequently used as an expression system for the production of recombinant proteins, and more recently also for the production of small metabolites (Marx et al. Microb Cell Fact 7:23 (2008)). *Pichia* has a high growth rate and is able to grow on a simple, inexpensive medium. *Pichia* can grow in either shake flasks or a fermenter, which makes it suitable for both small and large scale production. *Pichia pastoris* has recently been reclassified into a new genus, *Komagataella*, and been separated into three new species: *Komagataella pastoris, K. phaffii,* and *K. pseudopastoris* (Kurtzman C P. Int J Syst Evol Microbiol 55, 973-976. (2005)). Therefore, *Pichia pastoris* is a synonym for all three species, *K. pastoris, K. phaffii* and *K. pseudopastoris*. In accordance with previous literature, *Pichia pastoris* is used throughout this text, implicitly meaning any of the *Komagataella* species. Similarly, *Hansenula polymorpha* and *Pichia angusta* are synonyms.

In most cases, host cells are cultivated in fed batch processes for industrial production. The overall productivity of such a process is a function of the integral of biomass over time and the specific productivity ($q_P$) of the biomass. $q_P$ correlates with the specific growth rate ($\mu$), usually continuously increasing with increasing $\mu$. Therefore, high $q_P$ is achieved at high $\mu$, whereas the optimum biomass-time integral (A) is achieved with high initial and then very low $\mu$. This is reflected by the following formula to calculate the product yield (P) at constant $q_P$:

$$P = A \cdot q_P$$

Figure 1:
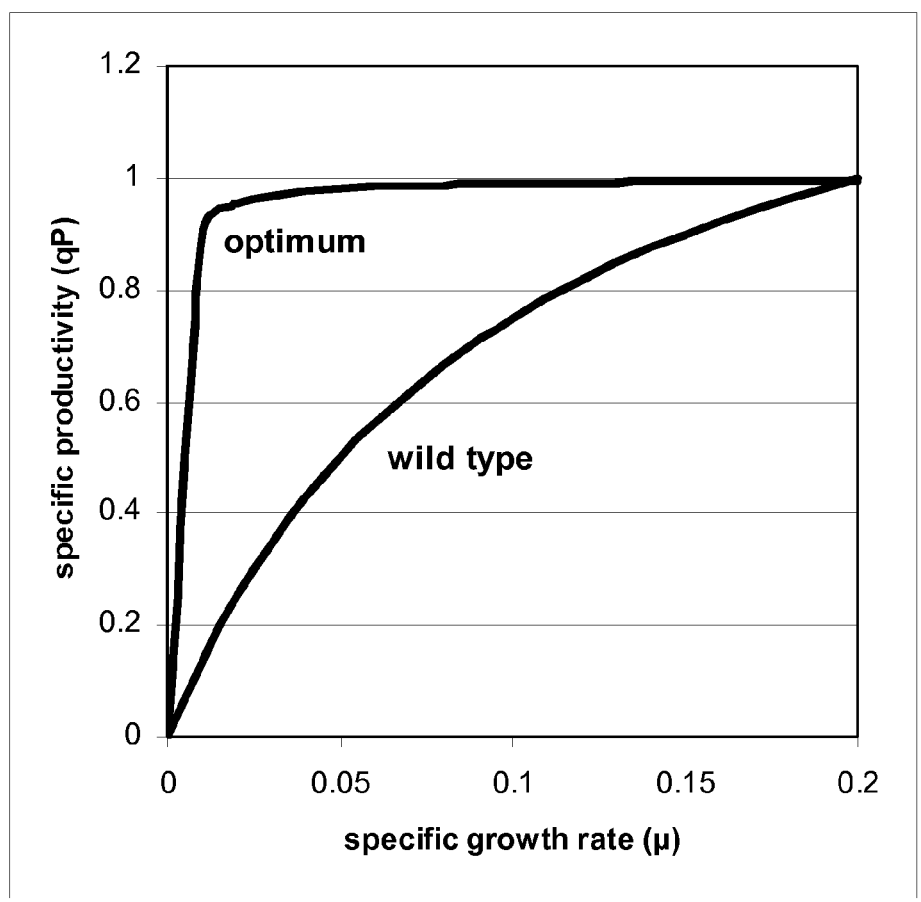

FIG. 1 shows the relation of $q_P$ and $\mu$ in *P. pastoris* (Maurer et al. 2006, Micr. Cell Fact. 5:37 doi: 10.1186/1475-2859-5-37).

Hence optimum productivity is achieved with a compromise of $\mu$, usually controlled in fed batch by limited substrate feed.

A typical case of fed batch process is the production of recombinant proteins with microorganisms or mammalian cells. While the description of product concentration in the cell mass is rather straight forward in the case of an intracellular product, it is more complex to predict the kinetics of a secreted product. A typical case for secretion systems are recombinant yeasts. As the production of many proteins in yeasts is quite cost sensitive, efforts are made to predict and control productivity, process time and product titers.

Approaches to optimize fed batch processes for the methylotrophic yeast *Pichia pastoris* have been described (Zhang et al. Biotechnol. Prog. 2005, 21: 386-393, Maurer et al. 2006, Micr. Cell Fact.).

The variable costs of a bioprocess correlate with the volumetric capacity of the required fermentation unit, and the process time this unit is required to produce a defined amount of the product. Thus, the volumetric productivity $Q_P$ is the most plausible target for optimization. At a given process time point t, $Q_P$ is defined as:

$$Q_P = P/(V \cdot t)$$

The cell cycle, or cell-division cycle, is the series of events that takes place in a cell leading to its division and duplication (replication).

Eukaryotic cell division proceeds through a highly regulated cell cycle comprising consecutive phases termed G1 (gap 1), S (synthesis), G2 (gap 2) and M (mitosis).

The phase G0 is called resting phase, where resting cells will, under certain circumstances or after receiving specific stimuli, initiate the synthesis of RNA and proteins (G1-phase) which are necessary to effectively carry out the multiplication of its DNA and the division of the cell into two daughter cells. Subsequently, DNA synthesis begins (S-phase); once the cell has duplicated its DNA, a second late-protein-synthesis period begins (G2-phase), which is the short phase preparing the cell for division (M-phase). G2 and M phase are both characterized by the double chromosome set and are often regarded together as G2+M phase.

During the brief phase of mitosis the eukaryotic cell separates the chromosomes in its cell nucleus into two identical sets in two daughter nuclei. Mitosis is generally followed immediately by cytokinesis, separating the cytoplasm into two daughter cells to provide for equal shares of the cellular components.

After cell division, each of the daughter cells begins the interphase of a new cycle. Cells that have stopped dividing, temporarily or not, are said to have entered a state of quiescence or senescence (G0).

Cell cycle progression is tightly regulated by defined temporal and spatial expression, localisation and destruction of a number of cell cycle regulators, which exhibit highly dynamic behaviour during the cell cycle. For example, at specific cell cycle stages some proteins translocate from the nucleus to the cytoplasm, or vice versa, and some are rapidly degraded. For details of known cell cycle control components and interactions, see Alberghina L, Coccetti P, Orlandi I. Systems biology of the cell cycle of *Saccharomyces cerevisiae*: From network mining to system-level properties. Biotechnol Adv. 2009 November-December; 27(6):960-78. The cell cycle process is complex and highly regulated. Errors in the cell cycle can either kill the cell through apoptosis or may lead to uncontrolled cell division, and in some cases to cancer.

Cell cycle analysis, mainly through the study of the distribution of cells throughout the G0/G1, S and G2/M cell cycle phases has proven to be of use in the analysis of tumor samples and the study of the proliferative response to different stimuli as well as in other areas.

The timing and inter-dependence of DNA replication (S-phase) and mitosis (M-phase) are controlled by oscillations in the activities of cyclin-dependent kinases (Cdks). Higher eukaryotes have multiple Cdks whereas in yeasts, cell cycle progression requires a single Cdk known as Cdc2 in fission yeast and Cdc28 in budding yeast. Waves of kinase activities are determined to a large extent by cell cycle-dependent synthesis and degradation of Cdk's regulatory cyclin subunits. Entry into M-phase depends on the appearance of B-type cyclins whose associated kinase activity promotes formation of the mitotic spindle. In budding yeast two pairs of related B-type cyclins appearing during S-phase (Clb3,4) and G2 (Clb1,2) are involved in formation and elongation of the spindle.

Cross et al. (Molecular Biology of the Cell (2005) 16:2129-2138) describe a quantitative behaviour of the eukaryotic cell cycle control system depending on the level of Clb2 expression. A loss of robustness of a Clb2 overexpressing system was predicted.

A series of fungal regulators, including cell cycle regulators, were described to improve the yield of fungal metabolite production (WO01/29073).

In an effort to improve protein expression from a producer cell line recombinant p21 or another cell cycle inhibitor protein has been co-expressed to enhance single cell productivity (WO02/099100A2). p21 is a universal inhibitor of cyclin kinases conferring stable and quantitative cell cycle arrest. Thus, care has to be taken to avoid triggering cell death or apoptosis in addition to its cytostatic effect.

WO0216590A2 discloses the extension of protein biosynthesis of a cell culture by switching the cells from a replicative to a productive state (RP switch), which is a pseudosenescent state. This can be accomplished by transformed cells conditionally expressing a cell cycle blocker arresting cell division. By preventing cell proliferation inducing differentiation to a senescence-like state, increased yields of bioproducts would be obtained.

Several methods can be used to synchronise cell cultures by halting the cell cycle at a particular phase, or separating cells of different phases. For example, serum starvation or addition of alpha factor would halt the cell in the G1 phase, mitotic shake-off, treatment with colchicine and treatment with nocodazole halt the cell in M phase and treatment with 5-fluorodeoxyuridine halts the cell in S phase.

A common measure to prolong the production phase of a cell culture is the limitation of substrates once biomass has grown to a certain extent. Likewise, additives to culture media are described to influence the cell cycle. KR100254810B1 discloses the addition of the antibiotic novobiocin to a CHO cell culture to increase the production of recombinant erythropoietin. Novobiocin serves as an inhibitor of early phases (pre-M) of the cell cycle.

Uchiyama et al. (Biotechnol Bioeng 54:262-271 (1997)) describe synchronous and arrested cultures of *Saccharomyces cerevisiae*. Synchrony was induced using both temperature-sensitive cdc mutants and inhibitors to arrest cell cycle progression to study cell cycle dependency. The cell cycle was stopped by switching the temperature from a permissive to a repressive one or else by the addition of a cell cycle inhibitor.

The universal blocking of cell growth and proliferation could effectively lead to a cell arrest and early apoptosis, resulting in a short production period of the cell culture. In general, the prolonged productivity in the absence of cell growth can hardly be maintained with state of the art technology.

It is the object of the present invention to prolong a highly productive phase of a cell culture to increase the yield of bioproducts.

SUMMARY OF THE INVENTION

The object is achieved by the provision of the embodiments of the present application.

According to the invention there is provided a method of preparing a high producer cell line for producing a polypeptide of interest (POI) in a cell culture, comprising genetically engineering a eukaryotic cell line to specifically cause prolongation of the G2+M cell cycle phase.

Specifically the method is for producing a recombinant polypeptide of interest (POI) in a cell culture, comprising genetically engineering a eukaryotic cell line
  to specifically cause prolongation of the G2+M cell cycle phase in a pre-culture phase, and
  to produce the POI in a producing phase following the pre-culture phase.

The cell-culture (i.e. cell line in culture) in the pre-culture phase particularly serves to grow the cells and establish the G2+M cell cycle phase as a steady state. By switching cell culture conditions to the producing phase, which is also referred to herein as the "production phase", the recombinant POI and eventually respective metabolites mediated by such POI, are effectively produced, still maintaining the advantageous GS+M cell cycle state. Thus, the staged culture method effectively provides for both, the enrichment of the cell culture for the cells capable of producing a high POI yield in the first stage, and the production of the POI in the second stage.

Specifically the cell line is a cell line having stably integrated in its genome an expression cassette to express a modulator of the cell cycle.

Preferably the cell line is engineered to modulate a cell cycle regulator, preferably by specifically overexpressing, activating, mutating, downmodulating, deleting, degrading or inhibiting a cell cycle regulator.

Preferred cell cycle regulators as used according to the invention are selected from the group consisting of the Cdk/cyclin complexes such as cyclin-dependent kinases (Cdk), G1 specific cyclins, G2/mitotic specific cyclins, and their transcription or degradation factors, such as Clb2, Clb1, Clb3-6, Cln1-3, Cdc6, Cdc14, Cdc20, Cdc28, Cdc48, Cdh1, Kar1, Mad2, MBF, Mcm1, Pds1, Rrp42, SBF, Sic1, Swe1, Swi5, Whi2.

According to a specific embodiment said cell line is a wild-card host cell line or a producer cell line that is engineered to produce a modulator of the cell cycle and said POI.

Specifically preferred POI are selected from the group consisting of serum proteins, such as an immunoglobulin or serum albumin, enzymes, hormones, signalling molecules, matrix proteins, fragments or derivatives thereof, or a polypeptide that mediates the production of a host cell metabolite.

The eukaryotic cell line as used according to the invention preferably is a fungal cell, preferably a yeast cell, such as a cell of the *Pichia* genus, in particular a cell of a strain of *P. pastoris*, or a higher eukaryotic cell, preferably a mammalian or a plant cell.

The invention further provides for the high producer cell line obtainable by a method according to the invention, having a specific productivity $q_P$ of at least 0.1 µg/(g·h) to produce said POI, preferably at least 0.1 mg/(g·h), more preferred at least 1 mg/(g·h), e.g. in cases of industrial or technical enzymes, in a cell culture under production conditions in industrial scale.

The invention further provides for the high producer cell culture obtainable by a method according to the invention, wherein at least 50% of the cells are in the G2+M phase over a process time that is at least 50% of the feed time.

Specifically the cell culture can be stably maintained at a steady state such G2+M distribution over a period of at least 10 hours.

According to specific aspects the cell culture is a fed-batch or continuous cell culture.

In a particularly preferred embodiment the inventive cell culture has a volumetric productivity $Q_P$ of at least 0.1 µg/(L·h), preferably at least 10 µg/(L·h), more preferred at least 0.1 mg/(L·h), even more preferred at least 1 mg/(L·h), e.g. in cases of industrial or technical enzymes, typically under production conditions in industrial scale, e.g. employing fed batch cultivation in reactor volumes of 100 L to 10 m³ or larger, employing typical process times of several days, or continuous processes in fermenter volumes of appr. 50-1000 L or larger, with dilution rates of appr. 0.05-0.15 h⁻¹. According to the invention there is further provided a method of increasing the yield of a recombinant POI production in a cell culture, comprising a) genetically engineering a eukaryotic production cell line to specifically cause prolongation of the G2+M cell cycle phase, b) cultivating said production cell line, and c) collecting a fraction of the cell culture containing the POI.

Specifically the method is for increasing the yield of a recombinant POI production in a cell culture, comprising a) genetically engineering a eukaryotic production cell line to specifically cause prolongation of the G2+M cell cycle phase, b) cultivating said production cell line in a pre-culture phase to obtain a steady state cell culture with a prolonged G2+M cell cycle phase, c) cultivating said steady state cell culture in a producing phase following said pre-culture phase to produce the POI, and c) collecting a fraction of the cell culture containing the POI.

The production cell culture in the producing phase is sometimes called main culture; an example is provided in the examples section below.

According to a further aspect of the invention there is provided a method of prolonging the production phase for producing a recombinant POI, i.e. a recombinant POI production phase of a eukaryotic production cell line in a cell culture, comprising genetically engineering the cell line to specifically cause prolongation of the G2+M cell cycle phase.

FIGURES

FIG. 1: Relation of $q_P$ and µ in *P. pastoris*.

Lower line: actual relation in wild type cells. Upper line: optimal relation for highest productivity.

This figure shows the functional relationship of the specific productivity of Fab expression and cell growth in a *P. pastoris* cell culture. The steepness of the curve indicates the ratio of $q_P$ to µ at a given µ and is a measure for the product titer that can be achieved at this given µ. Thus, the optimal yield may be achieved with a high initial growth rate followed by a steady state of the production phase over a prolonged period of time.

Figure 2:
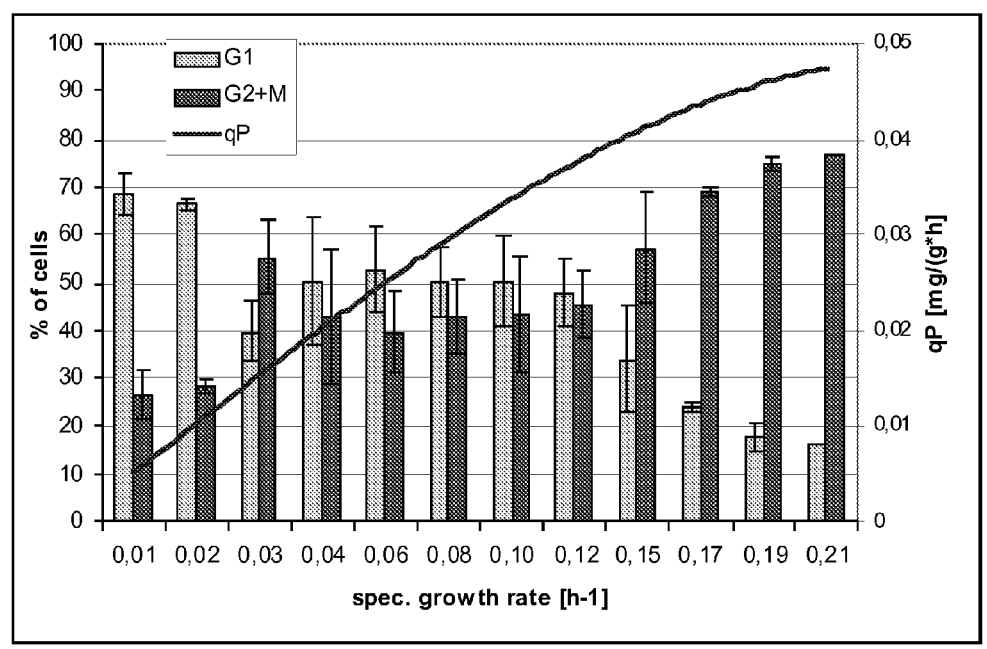

FIG. 2: Relation of $q_P$, µ and Cell Cycle Distribution in *P. pastoris*.

$q_P$ (black line) depends on µ according to a Monod function. The fractions of cells in G1 phase (single chromosome set, left bar) and G2+M phase (at least double chromosome set, right bar) indicate a positive correlation of qP with G2+M phase.

Figure 3:
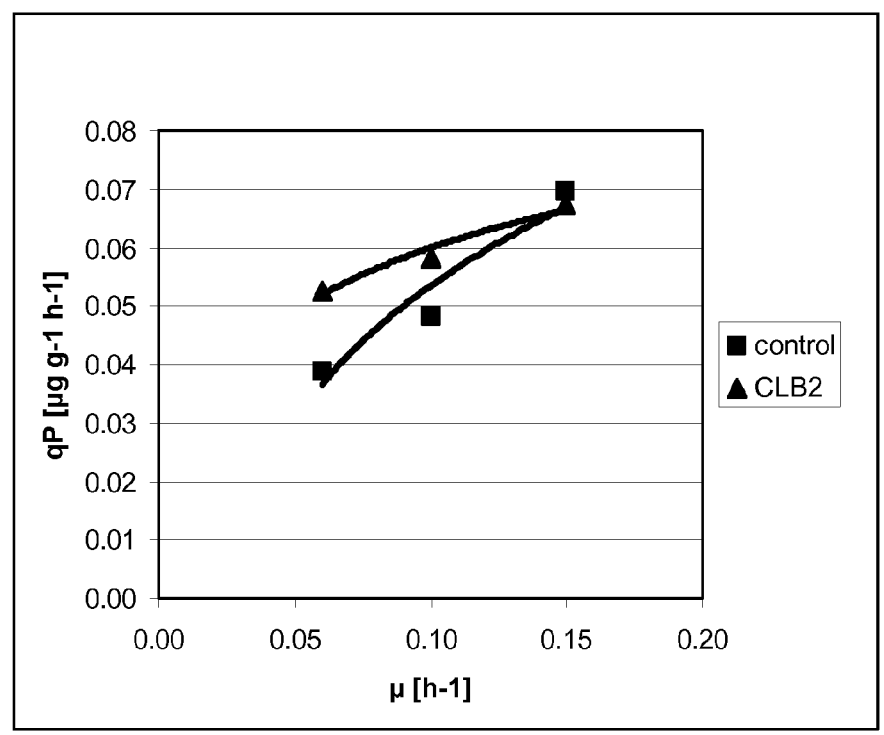

FIG. 3: Relation of $q_P$ and µ in Engineered *P. pastoris*.

Squares: control (wild type strain). Triangles: improved relation of Clb2 overexpression strain.

Figure 4:
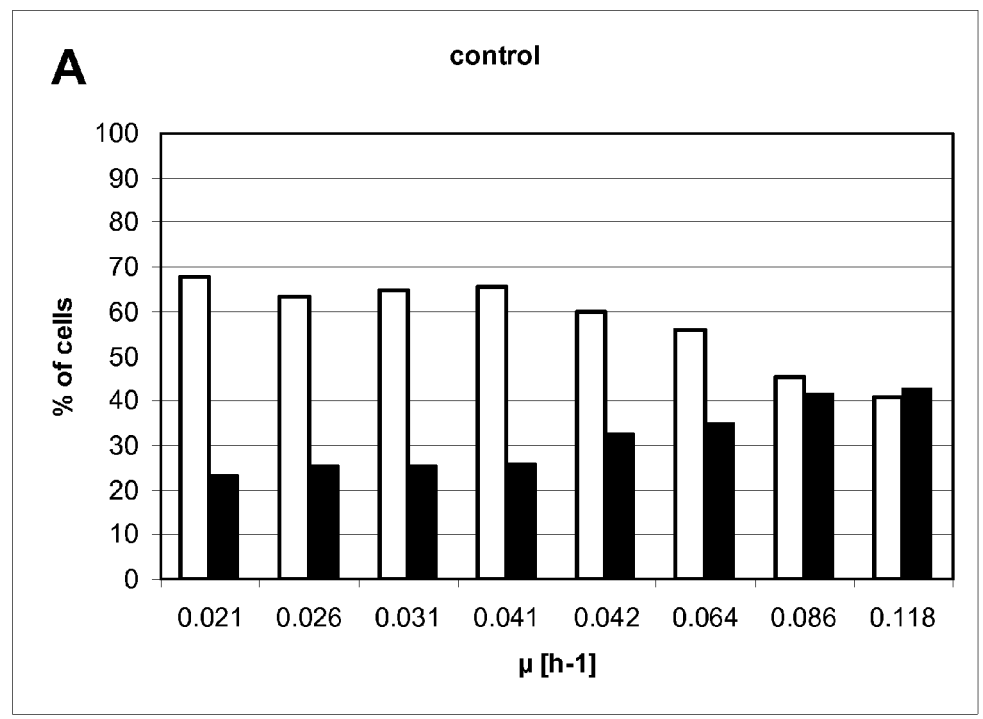
Figure 4:
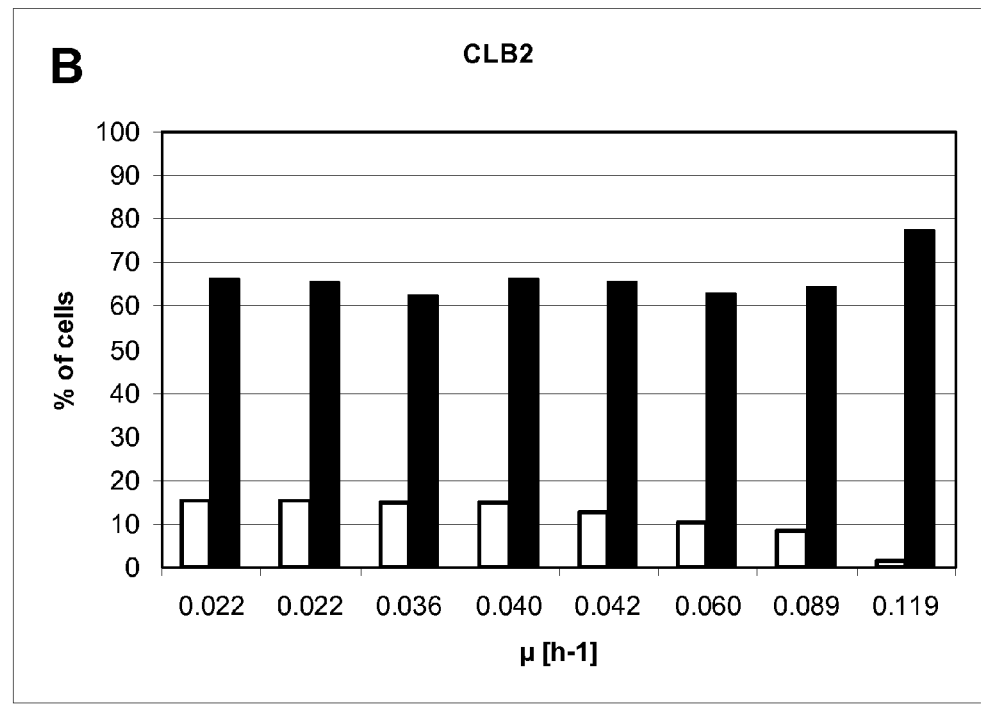

FIG. 4: Relation of µ and Cell Cycle Distribution in Engineered *P. pastoris*.

Left bars: fraction of cells in G1 phase, right bars: fraction of cells in G2+M phase.

DETAILED DESCRIPTION OF THE INVENTION

Therefore, the present invention is based on the advantageous effect that a specific prolongation of the G2+M phase or a relative increase of the number of eukaryotic cells in the G2+M phase within a cell culture provides for a highly productive biofactory device to produce a POI. This is effected by genetically engineering a cell line to obtain a recombined cell line with a genomic modification that would stably express an effector molecule causing said prolongation of the G2+M cell cycle phase. It surprisingly turned out that a respective cell culture could stably produce a POI with high yields at a low specific growth rate, thereby increasing the volumetric yield. Thus, the inventive producer cell line would not only be useful in a fed batch process, but also in a process of continued production, where the cell culture is maintained so that the fraction of G2+M cells are maintained at a high level over a prolonged production time.

The term "cell cycle modulator" as used according to the invention refers to effector molecules up-regulating or down-regulating cell-cycle inhibitors, kinases or other enzymes or co-factors of the cell-cycle control system. The term shall include cell cycle regulators and shall also refer to agonists or antagonists, activators or inhibitors of such effector molecules, cell-cycle inhibitors or the respective enzymes, which are actively involved in the cell cycle process. Cell cycle modulators may be physiological effectors of cell cycle control mechanisms, synthetic agents or chemicals, or biological substances with a proven modulating activity. Thus, cell cycle modulators have direct or indirect effects on the cell cycle regulation. Such compounds can be derived by the skilled person from the prior art, and eventually tested for their effects on the eukaryotic cell cycle by standard means.

The term "cell cycle regulator" shall refer to physiological, optionally endogenous substances actively involved in the cell cycle control of a eukaryotic cell.

The term "cell line" shall refer to an established clone of a particular cell type that has acquired the ability to proliferate over a prolonged period of time. The term "host cell line" refers to a cell line as used for expressing a recombinant gene to produce polypeptides or cell metabolites mediated by such polypeptides. A production host cell line is commonly understood to be a cell line ready-to-use for cultivation in a bioreactor to obtain the gene product in a production process.

The term "expression" or "expression system" or "expression cassette" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may also be integrated into the host chromosome.

"Expression vectors" or "vectors" used herein are defined as DNA sequences that are required for the transcription of cloned recombinant nucleotide sequences, i.e. of recombinant genes and the translation of their mRNA in a suitable host organism. Such expression vectors usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms plasmid and vector as used herein include autonomously replicating nucleotide sequences as well as genome integrating nucleotide sequences.

The term "eukaryotic host" shall mean any eukaryotic cell or organism, which may be cultivated to express a POI or a host cell metabolite. It is well understood that the term does not include human beings.

The term "G2+M cell cycle phase" also called G2/M phase or G2/M switch shall mean the short cell cycle phase following the synthesis phase (S), where the cells bear at least a double set of chromosomes and are prepared for division and processed for mitosis (M). The G2+M phase is followed by a phase characterized by the single set of chromosomes.

The term "polypeptide" refers to a protein or peptide that contains two or more amino acids, typically at least 3, preferably at least 20, more preferred at least 30, more preferred at least 50 amino acids. The term also refers to higher molecular weight polypeptides, such as proteins. Hereinafter the terms "polypeptide" and "protein" are interchangeably used.

The term "polypeptide of interest" or POI as used herein refers to a bioproduct produced in a host cell. More specifically, a polypeptide is produced, which does not naturally occur in the host cell, e.g. a heterologous protein. Other polypeptides may be native to the host cell, e.g. homologous proteins, but are produced, for example, by transformation with a self replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite produced by the host cell as mediated by a recombinantly expressed protein.

The term "wild-card host cell" shall mean a host cell, which is prepared by genetic engineering to comprise regulatory genes, such as those coding for cell cycle modulators, and which is ready to incorporate a gene of interest (GOI). The wild-card cell line is thus a preformed host cell line, which is characterized for its expression capacity of any desired POI. This follows an innovative "wild-card" strategy for the generation of producer cell lines, also called expression host cell line, for the production of biopharmaceuticals, e.g. using site-specific recombinase-mediated cassette exchange or homologous recombination. Such a new host cell facilitates the cloning of a GOI, e.g. into predetermined genomic expression hot spots within days in order to get reproducible, highly efficient production cell lines.

While determining the relationship of $q_P$, $\mu$, and other cellular properties of the yeast *Pichia pastoris*, it was surprisingly found that $q_P$ relates also to the cell cycle distribution of the host cells (FIG. 2). It turned out that a culture is more productive, when more cells are in the G2+M phase of the cell cycle. From these unexpected data it was concluded that better cell properties can be achieved, if the cells are engineered in a way that the distribution of cell cycle phases is changed at low $\mu$, so that more cells are in the G2+M phase of the cell cycle as compared to the wild type.

According to the invention host cells have thus been achieved which display high $q_P$ at low $\mu$, thereby prolonging the production phase of a cell culture producing a POI.

By the inventive method both parameters, $q_P$ and the product concentration, are preferably increased by at least 30%, preferably at least 40%, more preferred at least 50%.

The high productivity achieved according to the invention is specifically characterized by a $q_P/\mu$ ratio that is at least 3 µg product/g dry biomass.

The preferably obtained volumetric yield is in the range of 0.01 to 10 mg/(L·h), preferably over 1 mg/(L·h).

According to the invention cellular mutants with modified cell cycle control mechanisms, keeping cells in the G2+M cell cycle stage at a steady state for a prolonged period of time have been prepared and proven to achieve higher overall productivity and higher product concentrations as compared to the wild type.

By effectively prolongation of the relatively short G2+M cell cycle phase, a high percentage of G2+M cells in the host cell culture is preferably obtained. Preferred contents of G2+M staged cells as achieved in a production cell line as used in an industrial process according to the invention, are at least 50%, preferably at least 60%, more preferred at least 70%, even more preferred at least 80% up to 90%.

The steady state of the production phase would be achieved, if the desired share of the G2+M cells in the cell culture is maintained for a prolonged period of time. Preferably the steady state is maintained throughout the major part of the feeding time, preferably at least 50% of the feeding time, more preferred at least 60%, at least 70%, at least 80% or at least 90%. Typically, the steady state would be maintained over a process time of at least 10 h, preferably at least 15 h, more preferred at least 20 h in a fed batch process, which reflects the production phase of the cell culture. In a continuous process the process time could even be more prolonged.

Typically, the cell cycle status for cell populations can be determined by flow cytometry using fluorescent dyes which stain the DNA content of cell nuclei. Flow cytometry is as well suitable for examining the overall cell cycle distribution of cells within a population. By quantitative information on the DNA content of cells, the relative numbers of cells in the G1, S and G2+M phases of the cell cycle can be determined. Since the DNA content of cell nuclei varies through the cell cycle in a reasonably predictable fashion, it is possible to monitor the relative distribution of cells between different phases of the cell cycle. The technique usually would not precisely determine the cell cycle position of any individual cell due to ambiguity in assigning cells to G2 or M phases. Thus, the sum of the cell distribution in the G2+M stage is provided.

The target of genetic engineering preferably is a cell cycle regulator, which can be specifically overexpressed, activated, mutated, downmodulated, degraded or inhibited. Overexpression is, for example, achieved by expressing additional copies of a cell cycle regulator through the employment of a highly producing expression cassette or through introducing additional genes encoding the cell cycle regulator. Activation of kinases through phosphorylation is e.g. supported by the respective phosphorylation factors and cofactors. Cell cycle regulators may as well be modified to provide degradation resistant mutants. Exemplary means for downmodulating cell cycle regulators are employing silencing the respective genes using siRNA, antisense RNA or microRNA. Cell cycle regulators can also be degraded or inhibited by increasing the respective enzyme or inhibitor concentration or activity, e.g. by modulating the activity of specific proteases or kinases.

According to a specific embodiment a knock-out host cell may be used, which has a disruption of a gene encoding the cell cycle modulator, to down-modulate or eliminate their expression. A knock-out host cell may be produced by a method for knocking down, partially or completely, the respective gene. In those instances in which gene function or expression is downmodulated or eliminated, the resulting cell or organism can also be referred to as a knock-out. One embodiment of the method of producing knockdown cells and organisms comprises introducing into a cell or organism in which a gene is to be knocked down, RNA that targets the gene or its regulatory sequences and maintaining the resulting cell or organism under conditions under which antisense RNA occurs, resulting in degradation or inactivation of the respective mRNA or its regulatory sequences, thereby producing knockdown cells or organisms.

In another embodiment knockdown cells or organisms are produced by gene deletion, or promoter exchange, or by creation of temperature sensitive mutants.

To engineer a host cell for expressing a cell cycle modulator, an expression cassette can be stably integrated into the host cell genome. Suitable expression vectors comprising one or more of the cell cycle modulators may be constructed and their effect on the G2+M phase distribution may be determined by suitable means.

The obtained yield of a co-expressed POI can be compared to the wild-type to determine the effect of the modulator on the POI expression. A detailed description of the experimental procedure can be found in the examples below.

Preferably expression cassettes expressing a cell cycle modulator could be stably integrated into the host cell genome to prepare the host cell line according to the invention. According to a preferred embodiment, overexpression of the cell cycle regulator Clb2 or other cell cycle regulators, such as further G2/mitotic specific cyclins, cyclin-dependent kinases (Cdk), and their regulatory factors, such as Clb2, Clb1, Clb3-6, Cdc14, Cdc20, Cdc28, Mad2, Pds1, Rrp42, Whi2, is achieved by introducing a gene encoding such cell cycle regulator thereby increasing the copy number and respective activity. Thereby the cells have actually proven a higher qP at low μ as compared to the wild type.

By co-expressing a suitable cell cycle modulator and a POI, it is possible to provide for, under comparable conditions, at least the same, or at least about a 1.3-fold, or at least about 2-fold, or at least about a 3-fold, 4-fold, 5-fold, up to 10-fold yield increase relative to the wild type.

A wild-card cell line can be prepared by engineering the host cell to produce the respective cell cycle modulator as a first step. Then the wild-card cell line may be changed to a production cell line, which is engineered to express a POI.

Alternatively, the host cell can be recombined with genes encoding the cell cycle modulator and further genes of interest at the same time.

Furthermore, the host cell can also be engineered first to express a POI, and then be recombined with genes encoding a cell cycle modulator.

The POI can be any eukaryotic, prokaryotic or synthetic polypeptide. It can be a naturally secreted protein or an intracellular protein, i.e. a protein which is not naturally secreted. The present invention also provides for the recombinant production of functional homologues, functional equivalent variants, derivatives and biologically active fragments of natural proteins. Functional homologues are preferably identical with or correspond to and have the functional characteristics of a sequence.

A POI referred to herein may be, but is not limited to, a protein suitable as a biopharmaceutical substance like an antibody or antibody fragment, growth factor, hormone, enzyme, vaccine, or a protein which can be used for industrial application like e.g. an enzyme. A preferred POI is selected from the group of human serum proteins, such as an immunoglobulin or serum albumin, enzymes, hormones, signalling molecules, matrix proteins, fragments or derivatives thereof, or a polypeptide that mediates the production of a host cell metabolite. The POI is preferably a heterologous recombinant polypeptide or protein, which may advantageously be produced in a eukaryotic cell, preferably a yeast cell, preferably as secreted proteins. Examples of preferably produced proteins are immunoglobulins, immunoglobulin fragments, aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional analogue of any one of these proteins. In the present context, the term "functional analogue" is meant to indicate a polypeptide with a similar function as the native protein. The polypeptide may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

The recombinant POI is typically produced by recombinant techniques through a recombinant production cell line, comprising a recombinant gene of interest encoding such POI. It is specifically understood that such POI as produced according to the invention is not a cell cycle modulator or cell cycle regulator, but optionally produced as a recombinant product in addition to any recombinant cell cycle modulator produced by the same cell culture, as the case may be.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols or antibiotics, which can be obtained with increased yields following the expression of a recombinant protein or a POI according to the invention.

In general, the host cell, which expresses a recombinant product, can be any eukaryotic cell suitable for recombinant expression of a POI.

Examples of preferred yeast cells used as host cells according to the invention include but are not limited to the *Saccharomyces* genus (e.g. *Saccharomyces cerevisiae*), the *Pichia* genus (e.g. *P. pastoris*, or *P. methanolica*), the *Komagataella* genus (*K. pastoris, K. pseudopastoris* or *K. phaffii*), *Hansenula polymorpha* or *Kluyveromyces lactis*. Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudopastoris*.

The yeast producer organism preferably used according to the invention may be any suitable yeast organism which, on cultivation, produces large amounts of the heterologous protein or polypeptide in question. Preferred examples of suitable yeast organisms are strains selected from the yeast species *Saccharomyces cerevisiae*, *Saccharomyces kluyveri*, *Schizosaccharomyces pombe*, *Saccharomyces uvarum*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., and *Geotrichum fermentans*.

The most preferred yeast host cells are derived from methylotrophic yeast, such as from *Pichia* or *Komagataella*, e.g. *Pichia pastoris*, or *Komoagataella pastoris*, or *K. phaffii*, or *K. pseudopastoris*. Examples of the host include yeasts such as *P. pastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189, and DSMZ 70877 (German Collection of Microorganisms and Cell Cultures), but also strains from Invitrogen, such as X-33, GS115, KM71 and SMD1168. Examples of *S. cerevisiae* strains include W303, CEN.PK and the BY-series (EUROSCARF collection). All of the strains described above have been successfully used to produce transformants and express heterologous genes.

Examples of suitable higher eukaryotic cells, such as mammalian, insect or plant cells are CHO, Per.C6, HEK293, Sf-9, *Nicotiana tabacum* NT-1 or BY-2.

In general, the proteins of interest referred to herein may be produced by methods of recombinant expression well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982).

The nucleotide sequences that could be used for engineering the host cell as used according to the invention, which would provide for an improved recombinant protein production, can be obtained from a variety of sources. The origin of a promoter is preferably from a yeast cell, most preferably from methylotrophic yeast such as from the *Pichia* genus. The preferred homologous origin of the nucleotide sequence facilitates its incorporation into the host cell of the same genus, thus enabling stable production of a POI, possibly with increased yields in industrial manufacturing processes. Heterologous functionally equivalent nucleotide sequences from other suitable hosts can also be used.

Appropriate expression vectors comprise regulatory sequences suitable for expression of DNA encoding a heterologous polypeptide or protein in a eukaryotic host cell. Examples of regulatory sequences include promoters, operators, and enhancers, ribosomal binding sites, and sequences that control transcription and translation initiation and termination. The regulatory sequences may be operably linked to the DNA sequence to be expressed. For example, a promoter sequence is said to be operably linked to a coding sequence, if the promotor controls the transcription of the coding sequence.

According to the invention it is preferred to provide a *P. pastoris* host comprising regulatory sequences operably linked to the nucleotide sequence coding for the cell cycle modulator and to the nucleotide sequence coding for the POI, optionally further employing regulatory sequences operatively linked thereto.

According to a preferred embodiment the method according to the invention employs a recombinant nucleotide sequence encoding the POI, which is provided on a plasmid suitable for integration into the genome of the host cell, in a single copy or in multiple copies per cell. The recombinant nucleotide sequence encoding the POI may also be provided on an autonomously replicating plasmid in a single copy or in multiple copies per cell.

The preferred method according to the invention employs a plasmid, which is a eukaryotic expression vector, preferably a yeast expression vector. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector. A preferred yeast expression vector is for expression in yeast selected from the group consisting of methylotrophic yeasts represented by the genera *Hansenula*, *Pichia*, *Candida* and *Torulopsis*.

In the present invention, it is preferred to use plasmids derived from pPICZ, pGAPZ, pPIC9, pPICZalfa, pGAPZalfa, pPIC9K, pGAPHis or pPUZZLE as the vector.

To allow expression of a recombinant nucleotide sequence in a host cell, the expression vector may provide the recombinant nucleotide sequence with a functional promoter adjacent to the 5' end of the coding sequence, e.g. upstream from the signal peptide gene. The transcription is thereby regulated and initiated by this promoter sequence.

The promoter may be any suitable DNA sequence which shows transcriptional activity in the host cell and may be derived from genes encoding proteins either homologous or heterologous to the host. The promoter is preferably derived from a gene encoding a protein homologous to the host cell. The promoter can be an endogenous promoter or heterologous to the host cell.

Suitable promoter sequences for use with mammalian host cells may include but are not limited to promoters obtained from the genomes of viruses, heterologous mammalian promoters, e.g. the actin promoter or an immunoglobulin promoter, and heat shock protein promoters. The promoter is not limited to any particular species provided that they can function in eukaryotic host cells and in particular in yeast.

Further suitable promoter sequences for use with yeast host cells may include but are not limited to promoters obtained from genes that code for metabolic enzymes which are known to be present at high concentration in the cell, e.g. glycolytic enzymes like triosephosphate isomerase (TPI), phosphoglycerate kinase (PGK), glyceraldehyde-3-phosphate dehydrogenase (GAPDH), alcohol oxidase (AOX), lactase (LAC) and galactosidase (GAL).

Preferred examples of suitable promoters are the yeast promoters, which contain a DNA sequence that function as a promoter for gene transcription in yeast cells. Preferred examples are *S. cerevisiae* Mal, TPI, CUP, ADH or PGK promoters, or the *P. pastoris* glucose-6-phosphate isomerase promoter (PPGI), the 3-phosphoglycerate kinase promoter (PPGK) or glyceraldehyde-3-phosphate dehydrogenase promoter PGAP, the alcohol oxidase promoter (PAOX), formaldehyde dehydrogenase promoter (PFLD), isocitrate lyase promoter (PICL), translation elongation factor promoter (PTEF), and the promoters of *P. pastoris* enolase 1 (PENO1), triose phosphate isomerase (PTPI), alpha-ketoisocaproate decarboxylase (PTHI), ribosomal subunit proteins (PRPS2, PRPS7, PRPS31, PRPL1), heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-O2-oxidoreductase (PFET3), high affinity iron permease (PFTR1), repressible alkaline phosphatise (PPHO8), N-myristoyl transferase (PNMT1), pheromone response transcription factor (PMCM1), ubiquitin (PUBI4), single-stranded DNA endonuclease (PRAD2) and the promoter of the major ADP/ATP carrier of the mitochondrial inner membrane (PPET9).

In a preferred expression system the promoter is an inducible or a constitutive promoter.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

The procedures used to ligate the DNA sequences, e.g. coding for the cell cycle modulator and/or the POI, the promoter and the terminator, respectively, and to insert them into suitable vectors containing the information necessary for integration or host replication, are well known to persons skilled in the art, e.g. described by J. Sambrook et al., "Molecular Cloning 2nd ed.", Cold Spring Harbor Laboratory Press (1989).

It will be understood that one or more vectors, which use the genes encoding the cell cycle modulator and/or the POI as an integration target, may be constructed either by first preparing the DNA constructs containing the entire DNA sequence coding for the modulator and/or the POI and subsequently inserting the constructs into one or more suitable expression vectors, or by sequentially inserting DNA fragments containing genetic information for the individual genes followed by ligation.

Also multicloning vectors, which are vectors having a multicloning site, can be used according to the invention, wherein a desired gene can be incorporated at a multicloning site to provide an expression vector. In expression vectors, the promoter is placed upstream of the gene of the POI and regulates the expression of the gene. In the case of multicloning vectors, because the gene of the POI is introduced at the multicloning site, the promoter is placed upstream of the multicloning site.

Several different approaches for the POI expression and secretion in the eukaryotic host cell are preferred. Proteins are expressed, processed and secreted by transforming the eukaryotic organism with an expression vector harbouring DNA encoding the desired protein and at least one of the regulatory elements according to the invention, preparing a culture of the transformed organism, growing the culture and recovering the protein from the culture medium. The employed signal peptide may be the signal peptide according to the invention or an alternative one, e.g. a heterologous signal peptide or a hybrid of a native and a heterologous signal peptide. The function of the signal peptide is to allow the heterologous protein to be secreted to enter the endoplasmatic reticulum. The signal peptide is normally cleaved off in the course of this process. The signal peptide may be heterologous or homologous to the host organism producing the protein.

The DNA construct as provided to obtain a recombinant host cell according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the POI by hybridization using synthetic oligonucleotide probes in accordance with standard techniques. Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

Transformants according to the present invention can be obtained by introducing such a vector DNA, e.g. plasmid DNA, into a host and selecting transformants which express the POI or the host cell metabolite with high yields. Host cells are treated to enable them to incorporate foreign DNA by methods conventionally used for transformation of eukaryotic cells, such as the electric pulse method, the protoplast method, the lithium acetate method, and modified methods thereof. $P.$ $pastoris$ is preferably transformed by electroporation.

In another preferred embodiment, the yeast expression vector is able to stably integrate in the yeast genome, e.g. by homologous recombination.

It is understood that the methods disclosed herein may further include cultivating said recombinant host cells under conditions permitting the expression of the POI, preferably in the secreted form. A secreted, recombinantly produced POI or a host cell metabolite can then be isolated from the cell culture medium or other cell culture fractions and further purified by techniques well known to a person skilled in the art.

A preferred method according to the invention refers to the increase of the yield of a recombinant POI production in a cell culture, comprising a) genetically engineering a eukaryotic production cell line to specifically cause prolongation of the G2+M cell cycle phase, b) cultivating said production cell line, and c) collecting a fraction of the cell culture containing the POI.

The suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may be encompass a batch phase followed by a continuous cultivation phase at a low dilution rate. Preferred fermentation techniques are batch, fed batch or continuous cultivation.

Production conditions in industrial scale refer to e.g. fed batch cultivation in reactor volumes of 100 L to 10 $m^3$ or larger, employing typical process times of several days, or continuous processes in fermenter volumes of appr. 50-1000 L or larger, with dilution rates of appr. 0.05-0.15 $h^{-1}$.

The inventive high producer cell culture may as well be obtained without the influence of a recombinant cell cycle modulator, e.g. by specific cultivation techniques that would prolong the G2+M phase. Among these are controlled conditions of temperature, like temperatures below the optimum growth temperature, or of substrate feed, like intermittent feed control, or pulsing of substrates or chemicals, or others. Thereby the cell culture could be maintained at the desired G2+M distribution in the steady state as appropriate to support the high productivity of the cell culture.

A transformant host cell according to the invention obtained by transforming the cell with a gene encoding a cell cycle modulator and/or the POI genes may preferably first be cultivated at conditions to grow efficiently to a large cell number without the burden of expressing a heterologous protein. When the cell line is prepared for the POI expression and the cell culture has achieved a cell density of typically 10 g/L cell dry weight, cultivation techniques are chosen to produce the expression product.

It is preferred to cultivate the host cell line according to the invention in a bioreactor under growth conditions to obtain a cell density of at least 1 g/L cell dry weight, more preferably at least 10 g/L cell dry weight, preferably at least 50 g/L cell dry weight, but less than 150 or less than 200, preferably less than 100.

When the transformant is grown with an inductive stimulus, a cell cycle modulator may be activated to achieve the G2+M steady state, and the POI is expressed. An inductive stimulus is preferably heat, or addition of cadmium, copper, an osmotic pressure increasing agent, hydrogen peroxide, ethanol, methanol, methylamine or the like. Alternatively, gene expression may be stimulated by derepression, e.g. by the removal or dilution of glucose or thiamine, or the like.

Preferably the yeast is cultivated in a mineral medium with a suitable carbon source, thereby further simplifying the isolation process significantly. An example of a preferred mineral medium is one containing an utilizable carbon source (e.g. glucose, glycerol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

It is advantageous to provide for the POI production on a pilot or industrial scale. The industrial process scale would preferably employ volumina of at least 50 L, preferably at least 1 m$^3$, preferably at least 10 m$^3$, most preferably at least 100 m$^3$.

The POI is preferably expressed employing conditions to produce yields of at least 1 mg/L, preferably at least 10 mg/L, preferably at least 100 mg/L, most preferred at least 1 g/L.

The host cell according to the invention is preferably tested for its expression capacity or yield by at least one of the following tests: ELISA, activity assay, HPLC, or other suitable tests.

The transformed cells are cultivated under conditions suitable to effect expression of the desired POI, which can be purified from the cells or culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell and particular expression vector employed.

It is preferred that specific fractions of the cell culture are collected to obtain the POI as a bioproduct. Typically the cell culture supernatant would be collected, e.g. to obtain a secreted POI. Depending on the POI characteristics, it can be recovered from intracellular fractions or cell debris. For instance, the cultured transformant cells can be ruptured sonically or mechanically, enzymatically or chemically to obtain a cell extract containing the desired POI, from which the POI is isolated and purified. Secretion of the recombinant expression products from the yeast cells is generally advantageous for reasons that include facilitating the purification process, since the products can be recovered from the culture supernatant rather than from the complex mixture of proteins that results when yeast cells are disrupted to release intracellular proteins.

The desired compound typically can be isolated and purified using state of the art techniques.

As isolation and purification methods for obtaining a recombinant polypeptide or protein product, methods, such as methods utilizing difference in solubility, like salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used. Specific purification steps are preferably employed to separate any cell cycle modulator that is co-expressed and would contaminate the POI preparation.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

The isolated and purified POI can be identified by conventional methods such as Western blotting or assay of its activity. The structure of the purified compound can be defined by amino acid analysis, amino-terminal analysis, primary structure analysis, and the like. It is preferred that the compound is obtained in large amounts and with a high purity, thus meeting the necessary requirements for being used as an active ingredient in pharmaceutical compositions.

The preferred host cell line according to the invention maintains the genetic properties employed according to the invention, and the expression level remains high, e.g. at least at a μg level, even after about 20 generations of cultivation, preferably at least 30 generations, more preferably at least 40 generations, most preferred of at least 50 generations. The recombinant host cell is surprisingly stable, which is a great advantage when used for industrial scale protein production.

The present invention is described in further detail in the following examples, which are not in any way intended to limit the scope of the invention as claimed.

EXAMPLES

Example 1

Cell Cycle Distribution at Specific Growth Rates

To analyse *P. pastoris* cells at different specific growth rates, they were grown in chemostat cultures at a range of dilution rates between 0.01 h$^{-1}$ and 0.21 h$^{-1}$. Chemostat cultivation was initiated batch cultures had come to an end. Each dilution rate was maintained for at least five residence times, before samples were taken to determine biomass dry weight, Fab fragment concentration and cell cycle distribution.

Chemostat Medium GLU01:

1.0 g citric acid monohydrate, 55 g glucose monohydrate, 4.4 g (NH$_4$)$_2$HPO$_4$, 0.7 g MgSO$_4$*7H$_2$O, 1.7 g KCl, 0.01 g CaCl$_2$*2H$_2$O, 1.6 mL Trace Metal Solution (PTM1) and 1.0 mL biotin solution (0.2 g L$^{-1}$) were dissolved per 1000 mL ddH$_2$O, followed by sterile filtration.

Dry biomass concentration was determined by washing and drying the biomass of 10 mL aliquots of the culture. Fab fragment concentration was determined by ELISA as described by Dragosits et al. 2009 (J. Proteome Res. 2009 March; 8(3):1380-92). Specific productivity was calculated by dividing Fab concentration by dry biomass concentration and multiplying with the dilution rate.

For cell cycle phase distribution analysis, samples of ethanol fixated cells of each sample point were washed and treated with RNaseA. Then cells were sonicated and incubated in a propidium iodide solution to allow the reagent to enter the cells and stain the genomic DNA. Flow cytometry allows measuring of several thousand cells. An event count of 50.000 was used as the standard quantity. In case of a very low cell concentration in the remaining sample, this threshold had to be lowered. The data was evaluated with the help of the FCS Express Software. The percentage of cells being in G2+M phase of the cell cycle was calculated as follows: (% G2+M cells)/[(% G1 cells)+(% G2+M cells)]. As a result, the percentage of cells being in G1 phase is 100−(% G2+M cells). This calculation omits all cells that were not assigned to either G1 or G2+M phase.

Specific productivity $q_P$ and cell cycle phase distribution at different specific growth rates are shown in FIG. 3.

Example 2

Overexpression of CLB2 in P. pastoris and Determining the Cell Cycle Distribution at Specific Growth Rates a) Construction of Co-Overexpression Plasmids To generate a plasmid suitable for co-overexpression of CLB2 gene of P. pastoris in a strain already expressing a heterologous protein, the CLB2 gene was amplified by PCR from P. pastoris cDNA library. Non template coded P. pastoris Kozak sequence and restriction sites for SbfI and SfiI were added by using respective forward (5'-GATCCACCT-GCAGGCCATGTCTAATGTTCAGCCTAACGA-3', SEQ ID No. 1) and backward (5'-TCGGCCGAGGCGGCCCTA-CAAAATTGGATCCATGATGC-3', SEQ ID No. 2) oligonucleotide primer. SbfI and SfiI treated PCR products were cloned into pPuzzleKanR (SbfI and SfiI digested and treated with alkaline phosphatase).

The novel co-overexpression plasmid pPuzzleKanR-CLB2 was transformed into E. coli Top10 (Invitrogen). Restriction endonuclease digest and sequencing was done to verify the correct identity of the constructed plasmid.

b) Construction of P. pastoris Strains Co-Overexpressing Recombinant Human Antibody Fab Fragment 3H6 and a Novel Helper Factor Gene The plasmid pPuzzleKanR-CLB2, obtained from cloning procedure described in Example 2 step a) were used to transform a strain of P. pastoris pre-selected for the high level expression of recombinant human antibody Fab fragment 3H6 under the control of the GAP promoter (Dragosits et al. 2009, J Proteome Res. 2009 March; 8(3):1380-92). Selection was based on Zeocin resistance for the Fab fragment genes and Geneticin resistance for the helper factor genes.

To evaluate the effect of the co-overexpressed cell cycle regulator gene, the Fab fragment expressing strain was also transformed with a pPuzzleKanR plasmid without cell cycle regulator gene.

Example 3

Overexpression/Deletion of Other Cell Cycle Regulators to Shift the Cell Cycle a) For the overexpression of other cell cycle regulators expression vectors were constructed as described in example 2.a, except that the desired cell cycle regulator genes were amplified and cloned instead of CLB2. S. cerevisiae MAD2 and PDS1, and P. pastoris RRP42 were thus cloned into pPuzzleKanR to construct pPuzzleKanR-MAD2, pPuzzle-KanR-PDS1, and pPuzzleKanR-RRP42.

These plasmids were transformed into P. pastoris producing 3H$_6$Fab, as described in example 2.b).

b) Knock out of cell cycle regulator genes from the P. pastoris genome

Two fragments of the cell cycle regulator gene of appr. 350 bp length are amplified by PCR and cloned on both sides of the kanMX4 marker cassette conferring resistance to G418. After transformation of P. pastoris and selection for G418 resistance, deletion of part of cell cycle regulator gene is verified by PCR.

Example 4

Cultivation of a Cell Culture and Analysis of the Effect of Cell Cycle Regulator Overexpression Precultures of the strain overexpressing CLB2 (as described in example 2.b) in 2.5 mL YPD (20 g/L soy peptone (HY QUEST), 10 g/L yeast extract, 20 g/L glucose, pH 7.4) in 50 mL tubes were inoculated with cells from a plate. Next day, all main cultures (10 mL Synthetic shake flask medium in 50 mL tubes) were inoculated with an OD$_{600}$ of 0.1. Main culture media: (22 g citric acid monohydrate, 22 g glucose monohydrate, 3.15 g (NH$_4$)$_2$HPO$_4$, 0.492 g MgSO$_4$*7H$_2$O, 0.8040 g KCl, 0.0268 g CaCl$_2$*2H$_2$O, 1.47 mL Trace Metal Solution (PTM1) and 2.0 mL biotin solution (0.2 g L$^{-1}$) were dissolved per 1000 mL ddH$_2$O. The pH was set to 5 with KOH 25%, followed by sterile filtration.

Main cultures were started at an OD$_{600}$ of 0.1 and shaken at 170 rpm at room temperature. Optical density was measured after approximately 24 hours and the end after 48 hours. Supernatant samples for protein analysis were drawn at both points in time. Extracellular Fab concentration, analyzed by ELISA, was related to the culture's optical density after 24 and 48 hours of cultivation. Four transformants were cultivated per strain and compared to their respective control strain.

Average product per biomass: fold change of the CLB2 clones over vector controls:

| Time | fold change improvement |
|------|------------------------|
| 24 h | 2.8 |
| 48 h | 1.2 |

Example 5

DNA Content Analysis

Samples of ethanol fixated cells were taken during the exponential growth phase after 24 hours in the shake flask cultivation, and treated for DNA staining and flow cytometry analysis as described in Example 1. The distribution of cell cycle phases is shown in the table below.

| Strain | % cells in G1 | % cells in G2 + M |
|--------|---------------|-------------------|
| Wt control | 40 | 60 |
| CLB2 | 16 | 84 |

Example 6

Chemostat Cultivation

Chemostat cultivation was initiated for the PpCLB2 and the control strain after their batch cultures had come to an end. Each dilution rate was maintained for at least three residence times. Yeast dry mass, Fab3H6 titer and specific productivity are summarized in Table 1, and specific productivity vs. specific growth rate is displayed in FIG. 3.

Chemostat Medium GLU01:

1.0 g citric acid monohydrate, 55 g glucose monohydrate, 4.4 g $(NH_4)_2HPO_4$, 0.7 g $MgSO_4*7H_2O$, 1.7 g KCl, 0.01 g $CaCl_2*2H_2O$, 1.6 mL Trace Metal Solution (PTM1) and 1.0 mL biotin solution (0.2 g $L^{-1}$) were dissolved per 1000 mL dd$H_2O$, followed by sterile filtration.

TABLE 1

Chemostat cultivation at three distinct dilution rates

| | control | | | PpCLB2 | | |
|---|---|---|---|---|---|---|
| $\mu$ = D [h-1] | YDM [g L-1] | Fab 3H6 [μg mL-1] | qP [mg g-1 h-1] | YDM [g L-1] | Fab 3H6 [μg mL-1] | qP [mg g-1 h-1] |
| 0.06 | 26.68 | 17.27 | 0.039 | 26.58 | 23.346 | 0.053 |
| 0.1 | 27.25 | 13.15 | 0.048 | 27.47 | 15.964 | 0.058 |
| 0.15 | 27.49 | 12.78 | 0.07 | 27.63 | 12.427 | 0.067 |

Example 7

Fed Batch Fermentation of Wild Type and CLB2 Overexpression Clones

The data obtained from the chemostat samples were used to calculate qP as a function of $\mu$ in order to simulate a fed batch production process with a theoretical maximum of volumetric productivity $Q_P$ (Maurer et al. 2006 Microb. Cell Fact.). The optimized fermentation strategy consisted of different phases to perform the calculated growth kinetic. The batch phase was followed by an exponential feed phase with a growth rate of 0.15 $h^{-1}$ for rapid biomass production (8 hours or 5 hours, respectively) before $\mu$ is decelerated until the end of the process (additional 8 or 22 hours, respectively). The process was designed to reach a biomass of 100 g $L^{-1}$ and optimized for $Q_P$.

As for chemostat cultivation, feed was initiated within one hour after total substrate (glycerol) consumption in the batch. Fed batch medium (glucose) was pumped into the reactor according to a calculated feed function representing substrate demand for approximating the modelled growth curve for optimal product formation.

Samples were taken from each of the two parallel bioprocesses every two to three hours with high focus on simultaneity concerning time intervals and equal sample volumes which did not exceed 15-20 mL per sampling, including purging.

The two modelled fed batch protocols were performed twice for PpCLB2 strain and control strain, yielding four parallel fermentations, eight fermentations in total. Attention was paid to equal treatment of the parallel fed batches concerning elapsed time between pO2 peak and feed start as well as equidistant sampling and sample quantity. In the course of the control strain optimized protocols, aeration turned out to be insufficient after the upper stirrer limit of 1250 rpm was hit. To avoid a drop of the pO2 value, which had its setpoint at 20% and was controlled by stirrer activity, up to 25% of pure oxygen was added to the air flow as needed. Again, the parallel cultures were treated equally concerning aeration.

Example 8

Cell Cycle Phase Distribution in Fed Batch Fermentation Samples

In order to measure cell size or viability, samples were diluted in PBS and could be acquired directly on the BD FACS Calibur™ flow cytometer and analysed with the BD CellQuest™ software.

Samples meant for DNA content analysis had to be fixated in 70% ethanol. While few μL of high-density fed batch culture in 500 μL ethanol were sufficient for further sample treatment, up to 1 mL of low-density shake flask culture were pelleted by centrifugation and resuspended by adding an equal volume of ice-cold ethanol dropwise. In all cases, the cells had to be washed twice with PBS to remove ethanol, incubated with RNase A (35 U $ml^{-1}$) for one hour to digest dsRNA and washed again twice in PBS. The solution with the cells was then transferred into a FACS tube and sonicated in one burst for three seconds to break clumps of cells before mixed with an equal volume of PI solution (1:100 in PBS). After short vortexing, the cells were ready for being measured. Samples should ideally contain $1\times10^6$ cells or particles per mL.

Cell cycle phase distributions of the strain overexpressing CLB2, and the wild type strain, are shown in FIG. 4.

The invention claimed is:

1. A method of producing a recombinant polypeptide of interest (POI) in a cell culture, comprising genetically engineering a eukaryotic cell line to overexpress a cell cycle regulator selected from the group consisting of cyclin-dependent kinases (Cdk), G1 specific cyclins, G2/mitotic specific cyclins, Clb2, Clb1, Clb3-6, Cln1-3, Cdc6, Cdc14, Cdc20, Cdc28, Cdc48, Cdh1, Kar1, Mad2, MBF, Mcm1, Pds1, Rrp42, SBF, Sic1, Swe1, Swi5, and Whi2 and to specifically cause prolongation of the G2+M cell cycle phase in a cell culture, followed by producing the POI, wherein the POI is a heterologous recombinant polypeptide or protein.

2. The method according to claim 1, wherein said cell line is a cell line having stably integrated in its genome an expression cassette to express said cell cycle regulator.

3. The method according to claim 1, wherein said cell line is a wild-card host cell line or a producer cell line that is engineered to produce said cell cycle regulator and said POI.

4. The method according to claim 1, wherein said POI is selected from the group consisting of serum proteins, enzymes, hormones, signalling molecules, matrix proteins, fragments or derivatives thereof, or a polypeptide that mediates the production of a host cell metabolite.

5. The method according to claim 1, wherein said cell is a fungal cell.

6. A method of increasing the yield of a recombinant POI production in a cell culture, comprising
  a) genetically engineering a eukaryotic production cell line to overexpress a cell cycle regulator selected from the group consisting of cyclin-dependent kinases (Cdk), G1 specific cyclins, G2/mitotic specific cyclins, Clb2, Clb1, Clb3-6, Cln1-3, Cdc6, Cdc14, Cdc20, Cdc28, Cdc48, Cdh1, Kar1, Mad2, MBF, Mcm1, Pds1, Rrp42, SBF, Sic1, Swe1, Swi5, and Whi2 and to specifically cause prolongation of the G2+M cell cycle phase,
  b) cultivating said production cell line to obtain a steady state cell culture with a prolonged G2+M cell cycle phase,
  c) followed by cultivating said steady state cell culture to produce the POI, and
  d) collecting a fraction of the cell culture containing the POI, wherein the POI is a heterologous recombinant polypeptide or protein.

7. A method of prolonging a recombinant POI production phase of a eukaryotic production cell line in a cell culture, comprising genetically engineering the cell line to specifically cause prolongation of the G2+M cell cycle phase.

8. The method according to claim 4, wherein said serum proteins include immunoglobulin or serum albumin.

9. The method according to claim 5, wherein said cell is a yeast cell of the *Pichia* genus.

10. The method according to claim 9, wherein said call is a yeast cell of a strain of *P. pastoris*.

11. The method according to claim 1, wherein the cell cycle regulator is Clb2.

\* \* \* \* \*

SEQUENCE LISTING

<160> NUMBER OF SEQ ID NOS: 2

<210> SEQ ID NO 1
<211> LENGTH: 39
<212> TYPE: DNA
<213> ORGANISM: Artificial
<220> FEATURE:
<223> OTHER INFORMATION: primer

<400> SEQUENCE: 1
gatccacctg caggccatgt ctaatgttca gcctaacga          39

<210> SEQ ID NO 2
<211> LENGTH: 38
<212> TYPE: DNA

| | |
|---|---|
| <213> ORGANISM: Artificial<br><220> FEATURE:<br><223> OTHER INFORMATION: primer<br><br><400> SEQUENCE: 2<br><br>tcggccgagg cggccctaca aaattggatc catgatgc | 38 |